United States Patent [19]

Trinh et al.

[11] Patent Number: 5,714,445
[45] Date of Patent: Feb. 3, 1998

[54] ARTICLES CONTAINING SMALL PARTICLE SIZE CYCLODEXTRIN FOR ODOR CONTROL

[75] Inventors: Toan Trinh, Maineville; Dean Van Phan, West Chester, both of Ohio

[73] Assignee: The Procter & Gamble Company, Cincinnati, Ohio

[21] Appl. No.: 704,319

[22] Filed: Sep. 12, 1996

Related U.S. Application Data

[60] Continuation of Ser. No. 328,645, Oct. 25, 1994, abandoned, which is a division of Ser. No. 40,822, Mar. 31, 1993, Pat. No. 5,429,628.

[51] Int. Cl.$^6$ .................................................. C11D 3/20
[52] U.S. Cl. .................... 510/103; 510/102; 510/295; 510/438; 510/439; 510/507; 502/401
[58] Field of Search ......................... 502/501, 401, 502/404; 510/130, 295, 438, 439, 475, 507, 102, 103

[56] References Cited

U.S. PATENT DOCUMENTS

| | | | |
|---|---|---|---|
| 4,151,130 | 4/1979 | Adams | 260/17.4 |
| 4,186,743 | 2/1980 | Steiger | 128/284 |
| 4,267,166 | 5/1981 | Yajima | 424/48 |
| 4,426,292 | 1/1984 | Wernick et al. | 210/502.1 |
| 4,727,824 | 3/1988 | Ducharme et al. | 119/1 |
| 4,813,945 | 3/1989 | Le-Khac | 604/367 |
| 4,911,899 | 3/1990 | Hagiwara et al. | 423/118 |
| 5,139,687 | 8/1992 | Borgher, Sr. et al. | 252/8.6 |
| 5,234,610 | 8/1993 | Gardlik et al. | 363/8.6 |
| 5,348,667 | 9/1994 | Bacon et al. | 252/8.7 |
| 5,429,628 | 7/1995 | Trinh et al. | 604/359 |

FOREIGN PATENT DOCUMENTS

| | | |
|---|---|---|
| 0 347 746 A1 | 12/1989 | European Pat. Off. . |
| 0 389 015 A2 | 9/1990 | European Pat. Off. . |
| 0389 023 A2 | 9/1990 | European Pat. Off. . |
| 0 510 619 A1 | 10/1992 | European Pat. Off. . |
| 124452 | 7/1983 | Japan . |
| 128973 | 6/1986 | Japan . |
| 61-12564. | 6/1986 | Japan . |
| 63-165498 | 7/1988 | Japan . |
| 3-170415 | 7/1991 | Japan . |

OTHER PUBLICATIONS

H. Hashimoto, "Application of Cyclodextrins to Foods, Toiletries and Other Products in Japan," (1988) pp.1–12.
H. Hashimoto, "Studies in the Industrial Production and Application of Clclodextrins," Denpun Kagaku, vol. 36, No. 1, pp. 35–42 (1–15) (1989).

*Primary Examiner*—Glenn Caldarola
*Assistant Examiner*—Alexander G. Ghyka
*Attorney, Agent, or Firm*—Robert B. Aylor

[57] ABSTRACT

The present invention relates to compositions and articles such as catamenials, diapers, pantiliners, paper towels, tissues, underarm shields, etc., which minimize odor caused from body fluids through the incorporation of an effective amount of cyclodextrin, having a particle size of less than 12 microns. Combinations of small particle size cyclodextrins with other odor-controlling materials are also disclosed.

15 Claims, No Drawings

ARTICLES CONTAINING SMALL PARTICLE SIZE CYCLODEXTRIN FOR ODOR CONTROL

CROSS-RELATED TO RELATED APPLICATION

This application is a file wrapper continuation of our application Ser. No. 08/328,645, filed Oct. 25, 1994, now abandoned; which is a division of application Ser. No. 08/040,822, filed on Mar. 31, 1993, now U.S. Pat. No. 5,429,628.

TECHNICAL FIELD

The present invention relates to odor-controlling agents which are incorporated into articles such as catamenials, diapers, bandages, adult incontinence garments, and other disposable paper products, such as paper towels and napkins. The odor-controlling agents herein are designed to combat a broad spectrum of odoriferous materials, and are activated when they are most needed, e.g., in the presence of body fluids.

BACKGROUND OF THE INVENTION

A wide variety of fluid absorbent structures known in the art absorb body fluids such as blood, urine, menses, and the like, and are sanitary and comfortable in use. Disposable products of this type generally comprise fluid-permeable topsheet material, fluid absorbent core, and fluid-impermeable backsheet material. Various shapes, sizes and thicknesses of such articles have been explored in an attempt to make their use more comfortable and convenient.

Odor control in sanitary products has been under investigation for many years. Many body fluids have an unpleasant odor, or develop such odors when in contact with air and/or bacteria for prolonged periods.

Various odor-controlling agents have been disclosed in the literature. For example, U.S. Pat. No. 4,525,410, Hagiwara et al., issued Jun. 25, 1985, teaches zeolite particles (doped with bactericidal cations) assertedly stably held in a fibrous web by incorporating some portion of meltable fibers in the web, and applying heat. These compositions can be used as the "outside cover layer" in, e.g., "general sanitary goods".

U.S. Pat. No. 2,690,415, F. A. Shuler, issued Sep. 28, 1954, teaches particles of odor-absorbing materials uniformly affixed at the interstices of a permeable web by adhesive to provide an odor absorbent medium for, e.g., catamenials. Particulate carbon, silica gel and activated alumina are noted. Shifting/displacement of the particulates is assertedly avoided and the sheet is flexible.

ABSCENTS (odor-control molecular sieve from Union Carbide) for use in diapers and catamenials are specifically noted in Union Carbide brochure (A. J. Gioffre 1988). The brochure indicates that UC's market research shows potential benefits in such products. U.S. Pat. Nos. 4,795,482 and 4,826,497, relate to ABSCENTS used as an odor-controlling agent, generally, and in sanitary products, in particular.

Activated carbon is a very effective odor absorber, with average internal surface area of about 1000 $m^2/g$. However, with its intense black color, activated carbon is less readily incorporated into consumer products.

Zeolites have smaller surface area, in the range of about 400–800 $m^2/g$. They are white or have light color, and thus are aesthetically acceptable. However, zeolites may absorb the moisture in body fluids (i.e., water) over other fluids, which may compromise its effectiveness. Furthermore, activated carbon and zeolites have open structures, and continuously absorb airborne organic vapor, unless hermetically sealed. Therefore, during storage, these odor adsorbents can become saturated and less efficient before the products are used.

Some consumers prefer catamenial and diaper products, etc., that have a "scent signal" in addition to odor control. A "scent signal" is a positive perfume odor which signals the removal of odor during use of the product. This scent signal is normally difficult to provide because odor absorbents can react with and/or deplete the perfume in the article prior to use, and the absorbents themselves can become inactive.

A consumer's ability to notice their own body odor, both good and bad, decreases after prolonged exposure to the odor making it difficult for them to evaluate the efficacy of odor removal products. In other words, consumers become habituated to constant odors. Therefore, the positive odor is preferably fleeting and is delivered in "bursts" during use to avoid habituation to the positive signal. The "scent signal" signifies the removal of odor so the consumer can feel greater self-confidence.

SUMMARY OF THE INVENTION

Accordingly, the present invention provides an additional means for safely and effectively overcoming the deficiencies in the art by incorporating small particle size uncomplexed cyclodextrins for malodor control and optional moisture-activated encapsulated perfumes for an in use "burst of fragrance" or "scent signal."

Therefore, the present invention relates to compositions which minimize odor caused from bodily fluids, comprising:

I. an effective, odor-controlling amount of uncomplexed cyclodextrin, having a particle size of less than about 12 microns;

II. an effective amount of fluid-absorbing materials;

III. optionally, an effective amount of adjunct odor-controlling agent selected from the group consisting of:
  A. zeolite;
  B. activated carbon;
  C. kieselguhr;
  D. water-soluble antibacterial compound; and
  E. mixtures thereof; and IV. optionally, a moisture-activated encapsulated perfume which provides a scent signal indicating that the odor is being removed.

Free uncomplexed cyclodextrin absorbs malodor very effectively. In general, dry cyclodextrin powder is not effective and only absorbs malodor on its surface. Therefore, unlike absorbents with open structure, such as zeolites and activated carbon, dry cyclodextrin powder does not have the tendency to absorb airborne organic vapor before the product is used. But when "wetted" via urine, menses, or aqueous fluid in general, cyclodextrin is solubilized and thus can absorb odor more effectively by forming inclusion complexes with the malodor molecules.

In addition, small particle size cyclodextrin will increase the rate of solubilization and the surface area available to absorb odoriferous molecules and thus improve odor absorption efficacy.

Increasing the rate of absorption of odoriferous molecules is especially important when the amount of body fluids available to wet a substrate is small (e.g., as in consumer products for personal use, where odor may be generated by a small quantity of body fluids such as sweat, menses, urine, etc.) and when these fluids may already have a considerable amount of dissolved materials present.

For many personal use compositions, the activation of the uncomplexed, small particle size cyclodextrin should be as quick as possible. The improved speed of activation in many instances is necessary to provide a concentration of the uncomplexed cyclodextrin. When the volume or temperature of the fluid is low or the time available to effect odor absorption is limited, small particles are essential to provide any noticeable effect.

Uncomplexed cyclodextrin incorporated into consumer articles will more rapidly and effectively absorb odoriferous molecules if the particle size, in an amount that provides at least an effective, odor controlling amount of said uncomplexed cyclodextrin, is reduced to less than about 12 microns, preferably less than about 10, more preferably less than about 8, and even more preferably less than about 5, typically between about 0.001 and about 10, preferably between about 0.05 and about 5 microns.

The optional moisture-activated encapsulated perfume includes any encapsulated perfume system which will release the perfume when wetted by water. Preferably, moisture-activated encapsulated perfume includes cyclodextrin/perfume inclusion complexes, poly-saccharide matrix perfume microcapsules, and mixtures thereof.

Cyclodextrin/perfume inclusion complexes are very stable in the dry state. The cavity of the cyclodextrin molecules contain even very volatile perfume molecules with minimal perceptive airborne odor. Upon wetting by an aqueous fluid such as a body fluid, the perfume is released to provide a burst of fragrance. Therefore, a greater variety of perfumes can be used to accommodate a variety of consumer preferences.

In polysaccharide matrix perfume microcapsules, the perfume is dispersed as minute droplets in, e.g., a starch/dextrin solid cellular matrix. Moisture swells and softens the polysaccharide matrix to release the encapsulated perfume.

The present invention also encompasses articles of manufacture comprising the above composition. These articles contain an effective amount of uncomplexed small particle size cyclodextrin, generally at least about 0.01 g to about 20 g, preferably from about 0.02 g to about 15 g, more preferably from about 0.03 g to about 10 g per article. More uncomplexed, small particle size cyclodextrin can be used, as desired.

Small particle size uncomplexed cyclodextrin can be present in the fluid-retaining absorbent core or, alternatively, in the fluid-receiving front face (topsheet), especially in disposable paper products such as paper towels and napkins.

DETAILED DESCRIPTION OF THE INVENTION

The compositions and methods for controlling odors in the manner of this invention involve the use of uncomplexed, small particle size cyclodextrin materials, as described more fully hereinafter.

The articles which employ said uncomplexed, small particle size cyclodextrin odor-control technology can be prepared using constituents that are well-known in current commercial practice, and reference is made to the general sanitary products patent literature and trade catalogues for such items. Such items typically comprise a moisture absorbent "core" (e.g., pad) interposed between a "topsheet" and a "backsheet." Likewise methods and apparatus for assembling disposable diapers, catamenials, bandages, and the like are known in the art.

Other disposable articles such as paper towels and napkins consist only of a moisture absorbent layer (or layers), generally without a topsheet or a backsheet.

While the constituents used in the assembly of catamenials, disposable diapers, and the like, are well-known, the following may be mentioned by way of example. The present invention relates to the novel incorporation of uncomplexed, small particle size cyclodextrin into the matrix of these articles, rather than in the constituents of the articles, per se.

I CYCLODEXTRIN

As used herein, the term "cyclodextrin" includes any of the known cyclodextrins such as unsubstituted cyclodextrins containing from six to twelve glucose units, especially, alpha-, beta-, and gamma-cyclodextrins, and/or their derivatives, and/or mixtures thereof. The alpha-cyclodextrin consists of 6, the beta-cyclodextrin 7, and the gamma-cyclodextrin 8, glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. Nos: 3,426,011, Parmerter et al., issued Feb. 4, 1969; 3,453,257, 3,453,258, 3,453,259, and 3,453,260, all in the names of Parmerter et al., and all also issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use herein are methyl-beta-cyclodextrin, hydroxyethyl-beta-cyclodextrin, and hydroxypropyl-beta-cyclodextrin of different degrees of substitution (D.S.), available from Amaizo; Wacker Chemicals (USA), Inc.; and Aldrich Chemical Company. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company (beta-cyclodextrin/epichlorohydrin copolymers).

Alpha-, beta-, and gamma-cyclodextrin solids have "cage"-type crystalline structure. The packing of these cyclodextrin molecules within the crystal lattice is such that the cavity of one cyclodextrin molecule is blocked off on both sides by adjacent cyclodextrins, thereby producing isolated and closed cavities. These molecular arrangements are described in detail in *Cyclodextrin Technology*, Jozsef Szejtli, Kluwer Academic Publishers, 1988, page 6, incorporated herein by reference. In the dry state the isolated cavities are thus not readily accessible to airborne organic vapor, unlike other open-celled porous adsorbents such as activated carbon and zeolites. Therefore, surface area availability is essential for an effective malodor control performance by uncomplexed cyclodextrin powder. Upon solubilization of the cyclodextrins by the body fluids, the isolated cavities become available to form inclusion complexes with the odoriferous molecules. The availability of solubilized uncomplexed cyclodextrin is essential for an effective and efficient odor control performance.

The individual cyclodextrins can also be linked together, e.g., using multifunctional agents to form oligomers, polymers, etc. Examples of such materials are available commercially from Amaizo and from Aldrich Chemical Company (beta-cyclodextrin/epichlorohydrin copolymers).

The preferred cyclodextrin is beta-cyclodextrin. It is also desirable to use mixtures of cyclodextrins. Such mixtures can absorb odors more broadly by complexing with a wider range of odoriferous molecules. Preferably at least a major portion of the cyclodextrins are alpha-, beta- and/or gamma-cyclodextrins, more preferably alpha- and beta-cyclodextrins. Some cyclodextrin mixtures are commercially available from, e.g., Ensuiko Sugar Refining Company, Yokohama, Japan. Small particle size cyclodextrin can be prepared by mechanically grinding larger particles, e.g., those made by crystallization process, to provide the desired particle size. It is essential that at least an effective amount of the uncomplexed cyclodextrin be in small particle form.

I. A. Cyclodextrin Particle Sizes

In the normal production process, the cyclodextrins are isolated effectively and conveniently by fractional crystallization. This process normally produces crystalline solids having particle sizes of about 20 microns or larger. A beta-cyclodextrin sample obtained from the American Maize-Products Company is composed of about 95% of cyclodextrin with a particle size larger than 12 microns, about 88% of cyclodextrin with particle size larger than 20 microns, and with about 58% of cyclodextrin with particle size in the 49 to 118 micron range, as determined by a Malvern Particle and Droplet Sizer, Model 2600C, sold by Malvern Instruments, Inc., Southborough, Mass. Surface area availability of the uncomplexed cyclodextrin is essential for effective and efficient odor control performance by cyclodextrin powder. By way of exemplification, for particles of essentially the same shape, all particles having the same exact size, one gram of cyclodextrin of 5 micron size has the same surface area as 100 g of cyclodextrin of 50 micron size, and 1 g of cyclodextrin of 3 micron size has the same surface area as 1600 g of cyclodextrin of 120 micron size.

The small particles of this invention, e.g., those having a particle size of less than about 12 microns, preferably less than about 10 microns, more preferably less than about 8 microns, and even more preferably less than about 5 microns, are essential for providing a quick pickup of odor when the cyclodextrin is wetted.

These small particles of the invention are conveniently prepared by grinding techniques. Cyclodextrin with large particle sizes can be pulverized to obtain the desired smaller particles of less than about 12 microns by using, e.g., a fluid energy mill. Examples of fluid energy mills are the Trost Air Impact Pulverizers Jet Mill (Research Model Gem-T), sold by Garlock Inc., Plastomer Products, Newtown, Pa.; the Micronizer fluid energy mills sold by Sturtevant, Inc., Boston, Mass.; and the Spiral Jet Mill sold by Alpine Division, MicroPul Corporation (Hosokawa Micron International, Inc.), Summit, N.J.

Another preferred method is an in situ and rapid crystallization wherein the substrate is impregnated with an aqueous solution of, e.g., uncomplexed beta-cyclodextrin. Upon drying, the cyclodextrin crystallizes out as small particles, adhering to the substrate and is immobilized on said substrate.

As used herein, the particle size refers to the largest dimension of the particle and to the ultimate (or primary) particles. The size of these primary particles can be directly determined with optical or scanning electron microscopes. The slides must be carefully prepared so that each contains a representative sample of the bulk cyclodextrin. The particles sizes can also be measured by any of the other well-known methods, e.g., wet sieving, sedimentation, light scattering, etc. A convenient instrument that can be used to determine the particle size distribution of the dry cyclodextrin powder directly (without having to make a liquid suspension or dispersion) is the Malvern Particle and Droplet Sizer, Model 2600C, sold by Malvern Instruments, Inc., Southborough, Mass. Some caution should be observed in that some of the dry particles may remain agglomerated. The presence of agglomerates can be further determined by microscopic analysis. Some other suitable methods for particle size analysis are described in the article "Selecting a particle size analyzer: Factors to consider," by Michael Pohl, published in Powder and Bulk Engineering, Volume 4 (1990), pp. 26–29, incorporated herein by reference. It is recognized that the very small particles of the invention can readily aggregate to form loose agglomerates that are easily broken apart by either some mechanical action or by the action of water. Accordingly, particles should be measured after they are broken apart, e.g., by agitation or sonication. The method, of course, should be selected to accommodate the particle size and maintain the integrity of the complex particles, with iterative measurements being made if the original method selected proves to be inappropriate. Care should also be taken to avoid contact of the cyclodextrin particles with excess water to prevent premature particle dissolution.

II. Substrates

The substrates useful herein can be any solid material that can carry and release the cyclodextrin as needed. They comprise, for example, solid particulates including solid absorbent particulates, fibrous absorbent materials, hydrogel forming absorbent gelling materials, paper, woven fabrics, nonwoven fabrics, natural fibers, synthetic fibers, polymeric films including formed polymeric films, formed polymeric particles, or mixtures thereof. Cellulosic solids are especially desirable as natural biodegradable substrates. Preferred substrates are solid particulates, fibrous absorbent materials, absorbent gelling materials, woven and nonwoven fabrics, films, and papers.

Desirable absorbent paper substrates are disclosed in U.S. Pat. Nos.: 3,905,863, Ayers, issued Sep. 16, 1975; 3,974,025, Ayers, issued Aug. 10, 1976; 4,191,609, Trokhan, issued Mar. 4, 1980; 4,440,597, Wells et al., issued Apr. 3, 1984; 4,529,480, Trokhan, issued Jul. 16, 1985; and 4,637,859, Trokhan, issued Jan. 20, 1987, all of said patents being incorporated herein by reference.

Some cyclodextrin-containing substrates of this invention can be used directly as absorbent articles, such as cyclodextrin-containing paper towels and napkins. Other articles of manufacture of this invention, such as catamenials, disposable diapers, and adult incontinence garments, typically comprise a moisture absorbent "core" (e.g., pad) interposed between a "topsheet" and a "backsheet." The cyclodextrin-containing substrate can constitute or be part of, e.g., the absorbent core, the topsheet, or both.

II. A. Fluid Absorbent Material

Fluid absorbent material can be any material which is generally compressible, conformable, non-irritating to the wearer's skin, and which is capable of absorbing and retaining fluids.

The fluid absorbent material can be constructed from any of a variety of materials commonly used in disposable absorbent articles. These materials are described in the hereinbefore incorporated patents. Examples of suitable absorbent materials include creped cellulose wadding, cotton fluff, citric acid cross-linked cellulose pulp disclosed in U.S. Pat. Nos.: 5,190,563, issued Mar. 2, 1993; 5,183,707, issued Feb. 2, 1993; and 5,137,537, issued Aug. 11, 1992, all issued to Herron et al., synthetic fibers disclosed in U.S. Pat. No. 4,578,414, Sawyer, issued Mar. 25, 1986; absorbent foams, absorbent sponges, super-absorbent composites, superabsorbent foam, and super absorbent polymers. A preferred fluid absorbent material is comminuted and air-laid wood pulp fibers commonly referred to as absorbent fluff. An absorbent fluff having a density of from about 0.05 g to about 0.175 g per cm$^3$ is generally acceptable.

More preferred fluid absorbent materials are the absorbent gelling materials. As is well known in the art, fluid absorbent gelling materials (sometimes referred to as "AGM" or "super-sorbers") are broadly used in fluid absorbent articles. In general, such AGM's have been used only for their fluid-absorbing properties. Such materials form hydrogels on contact with water (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred fluid absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. The hydrolyzed polyacrylic acid grafted starch materials are of this latter type. Thus the preferred fluid absorbent gelling materials include hydrolyzed polyacrylonitrile grafted starch, hydrolyzed polyacrylate grafted starch, polyacrylates, maleic anhydride-iso-butylene copolymers and combinations thereof. Especially preferred fluid absorbent gelling materials are the hydrolyzed polyacrylates and hydrolyzed polyacrylate grafted starch.

Whatever the nature of the polymer components of the preferred fluid absorbent gelling materials, such materials will in general be slightly cross-linked. Cross-linking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example: (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Cross-linking agents of the foregoing types are described in greater detail in U.S. Pat. No. 4,076,663, Masuda et al., issued Feb. 28, 1978. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the absorbent gelling materials used herein.

The preferred, slightly cross-linked, hydrogel-forming absorbent gelling materials will generally be employed in their partially neutralized form. For purposes described herein, such materials are considered partially neutralized when at least about 25 mole percent, and preferably at least about 50 mole percent of monomers, and more preferably at least about 75 mole percent, used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization." Typically, commercial fluid absorbent gelling materials have a degree of neutralization somewhat less than 90%.

The preferred fluid absorbent gelling materials used herein are those which have a relatively high capacity for imbibing fluids encountered in the fluid absorbent articles; this capacity can be quantified by referencing the "gel volume" of said fluid absorbent gelling materials. Gel volume can be defined in terms of the amount of synthetic urine absorbed by any given fluid absorbent gelling agent buffer and is specified as grams of synthetic urine per gram of gelling agent.

Gel volume in synthetic urine (see Brandt et al., below) can be determined by forming a suspension of about 0.1–0.2 parts of dried fluid absorbent gelling material to be tested with about 20 parts of synthetic urine. This suspension is maintained at ambient temperature under gentle stirring for about 1 hour so that swelling equilibrium is attained. The gel volume (grams of synthetic urine per gram of fluid absorbent gelling material) is then calculated from the weight fraction of the gelling agent in the suspension and the ratio of the liquid volume excluded from the formed hydrogel to the total volume of the suspension. The preferred fluid absorbent gelling materials useful in this invention will have a gel volume of from about 20 to 70 grams, more preferably from about 30 to 60 grams, of synthetic urine per gram of absorbent gelling material.

Another feature of the most highly preferred fluid absorbent gelling materials relates to the level of extractable polymer material present in said materials. Extractable polymer levels can be determined by: (1) contacting a sample of preferred fluid absorbent gelling material with a synthetic urine solution for a substantial period of time (e.g., at least 16 hours) to reach extraction equilibrium; (2) filtering the formed hydrogel from the supernatant liquid; and (3) determining the polymer content of the filtrate. The particular procedure used to determine extractable polymer content of the preferred fluid absorbent gelling agent buffers herein is set forth in U.S. Pat. No. 4,654,039, Brandt, Goldman and Inglin, issued Mar. 31, 1987, Reissue No. 32,649. The fluid absorbent gelling materials which are especially useful in the fluid absorbent articles herein are those which have an equilibrium extractables content in synthetic urine of no more than about 17%, preferably no more than about 10% by weight of the fluid absorbent gelling material.

The fluid absorbent gelling materials hereinbefore described are typically used in the form of discrete particles.

Such fluid absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of fluid absorbent gelling material particles may also be used.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics stand-point. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

The amount of fluid absorbent gelling material particles used in fluid absorbent cores will depend upon the degree of fluid absorbent capacity desired, and will generally comprise from about 2% to about 50% by weight of the fluid absorbent core, more typically from about 5% to about 20% by weight of the fluid absorbent core.

When fluid absorbent gelling material particles are to be used in the cores of the fluid absorbent articles herein, such cores can be prepared by any process or technique which provides a web comprising a combination of the fibers and the gelling material particles. For example, web cores can be formed by air-laying a substantially dry mixture of hydrophilic fibers and fluid absorbent gelling material particles and, if desired or necessary, by densifying the resulting web. Such a procedure is described more fully in U.S. Pat. No. 4,610,678, Weisman and Goldman, issued Sep. 9, 1986. As indicated in this U.S. Pat. No. 4,610,678, the air-laid webs formed by such a procedure will preferably comprise substantially unbonded fibers and will preferably have a moisture content of 10% or less.

Another example combining the fibers and the gelling material particles is a tissue laminate. Such a fluid absorbent core is described more fully in U.S. Pat. Nos: 4,950,264, Osborn, issued Aug. 21, 1990; 5,009,653, Osborn, issued Apr. 23, 1991; WO 93/01785, Osborn et al., published Feb. 4, 1993, "Stretchable Absorbent Articles;" and WO 93/01781, Johnson et al., published Feb. 4, 1993, "Curving Shaped Absorbent Articles," all of said patents incorporated herein by reference. As indicated in these references, glue is applied to an air-laid, latex-bonded tissue and absorbent gelling material is added and then the tissue is folded over.

The density of the fluid absorbent cores which comprise webs of hydrophilic fibers and fluid absorbent gelling material particles can be of importance in determining the fluid absorbent properties of the cores and of the fluid absorbent articles in which such cores are employed. The density of such fluid absorbent cores herein will preferably be in the range of from about 0.06 to about 0.3 g/cm$^3$, and more preferably within the range of from about 0.09 to about 0.22 g/cm$^3$. Typically the basis weight of the fluid absorbent cores herein can range from about 0.02 to 0.12 g/cm$^2$.

Density values for cores of this type can be calculated from basis weight and caliper. Caliper is measured under a confining pressure of 0.137 psi (0.94 kPa). Density and basis weight values include the weight of the fluid absorbent gelling materials and the odor-control material. Density of the cores herein need not be uniform throughout the core. Within the density ranges set forth above, the cores can contain regions or zones of relatively higher or relatively lower density.

The size of the fluid absorbent element is dictated by the exact product design selected.

II. B. Front-Face Material (Topsheet Material)

The finished articles herein will typically be provided with a fluid-receiving facing material. The front-face ("topsheet") material used herein can be any compliant, soft-feeling, non-irritating (to the wearer's skin) planar material. It functions to contact the wearer's skin, to receive fluid discharges, to allow the discharges to pass readily therethrough into the absorbent element, and to isolate the wearer's skin from the fluids in the absorbent element.

The topsheet can be porous paper made from natural or synthetic fibers or mixtures thereof, non-woven fabric made from the natural or synthetic fibers or mixtures thereof, apertured plastic film, porous foam, or the like.

A preferred topsheet is spun bonded non-woven polyester fabric made from fibers of from about 2.2 to about 2.5 denier, having a basis weight of about 17 g per square meter (m$^2$). Another preferred topsheet material has a basis weight of 22 g per m$^2$ and comprises about 65% by weight staple length, 1.5 denier polyester fibers (such as Kodel type 411 polyester fibers as sold by Tennessee Eastman Corporation, Kingsport, Tenn.); about 15% crimped, staple length 1.5 denier rayon fibers; and about 20% acrylic copolymer binder (such as Celanese CPE 8335 as sold by Celanese Corporation, Charlotte, N.C.). "Staple length" refers to fibers having a length of at least about 15 mm.

Still another preferred topsheet is constructed from polypropylene fibers which have been carded and thermally bonded in a spaced-apart pattern. Fibers about 3.8 cm long and of from about 1.5 to about 3.0 denier are suitable. A preferred topsheet of this type has a basis weight of about 24 g per m$^2$. Suitable topsheets can also be constructed from apertured plastic films such as those described in U.S. Pat. Nos. 4,342,314, Radel and Thompson, issued Aug. 3, 1982; 4,341,217, Ferguson and Landrigan, issued Jul. 27, 1982; 4,324,246, Mullane and Smith, issued Apr. 13, 1982; and 3,929,135, Thompson, issued Dec. 30, 1975, all of these patents being incorporated herein by reference.

For example, according to the process of U.S. Pat. No. 4,324,246, supra, a sample of thermoplastic material such as 0.0038 cm thick polyethylene film is heated above its softening point. (The softening point is the temperature at which the thermoplastic material can be formed or molded and is less than the melting point of the material.) The heated thermoplastic material in sheet form is then brought into contact with a heated forming screen. The forming screen is preferably an apertured wire mesh screen having the desired aperture size, pattern and configuration. A vacuum is used to draw the heated film against the forming screen, thereby forming the film into the desired pattern and having the desired hole sizes. While the vacuum is still being applied to the film, a jet of hot air is passed over the film. The hot air jet perforates the film in a pattern corresponding to the pattern and size of apertures in the forming screen.

Fluid-permeable sheets prepared in the manner of U.S. Pat. No. 4,324,246, supra, are conveniently referred to as "formed films." The caliper of such films is important since, if the caliper is too great, liquid may accumulate in the apertures and not readily pass therethrough. For the manufacture of fluid absorbent articles such as diapers, catamenials, incontinence articles, and the like, the sheets typically have a caliper of less than about 0.075 cm, or preferably less than about 0.064 cm.

Another formed-film sheet material useful herein is the resilient, 3-dimensional web exhibiting a fiber-like appearance and tactile impression, comprising a fluid-impervious plastic material, with said web having a multiplicity of apertures, the apertures being defined by a multiplicity of intersecting fiber-like elements, all as disclosed in U.S. Pat. No. 4,342,314, supra. The Radel and Thompson sheet materials can be prepared using hydrophobic plastics such as polyethylene, polypropylene, PVC, and the like, and are well-known for use in fluid absorbent products such as catamenials, and the like.

Yet another type of sheet material useful herein is described in U.S. Pat. No. 3,929,135, supra, and consists of hydrophobic polymer films having holes which are in the form of tapered capillaries. These "tapered capillary" sheets are also known for use in fluid absorbent articles, including adult incontinence articles. They may be prepared from various hydrophobic polymers, as mentioned hereinabove; typically, low density polyethylene having thickness of from 0.0025 to 0.0051 cm is employed.

Reference to U.S. Pat. No. 3,929,135, supra, can be made in order to further visualize tapered capillary sheets. In use, the apices of the capillaries in such tapered capillary topsheets are in contact with the underlying fluid absorbent core material. Generally, tapered capillaries are in the form of a frustrum of a conical surface, but it is to be understood that any generally tapered structure, such as a frustrum of a pyramid or the like with a triangular, square, or polygonal base, is within the term "tapered capillary"; circular tapered capillaries, however, are used in this description for convenience. It is also to be understood that the tapered capillaries can be asymmetric (i.e., the angle of taper on one side can be different from that on another side) and that the angle of taper can change continuously (i.e., be curved) over the distance from base to apex. In the latter case, the angle of taper is defined as the angle of the tangent to the side of the capillary at its point of minimum apex opening dimension. The angle of taper suitable for use in topsheets according to the practice of this invention is from about 10° to about 60°.

Base opening dimension of the capillaries is defined as the maximum open measurement in the plane of topsheet at said tapered capillary. Apex opening dimension is defined as the maximum open measurement in the apex of said tapered capillary, which apex is remote from the plane of the topsheet. When the tapered capillary is in the form of a frustrum of a conical surface, the base and apex opening dimensions are, respectively, the base diameter and the apex diameter. Base diameter and apex diameter are herein-after used interchangeably with, respectively, base opening dimension and apex opening dimension.

The tapered capillary apex diameter is a diameter which will allow liquid to readily pass from the surface of the topsheet to the underlying fluid absorbent core. The apex diameter is from about 0.004 to about 0.100 inch (0.010 to 0.254 centimeter), preferably from about 0.005 to about 0.020 inch (0.013 to 0.051 centimeter).

The tapered capillary base diameter is selected to satisfy two criteria. The first of these is the subjective feel of the surface of the topsheet which contacts the skin of the user. It has been discovered that polyethylene can be made to exhibit pleasing, clothlike, non-waxy attributes when the base diameter is within the range from about 0.006 to about 0.250 inch (0.015 to 0.635 centimeter). Preferably, the base diameter should be within the range of from about 0.030 to about 0.060 inch (0.076 to 0.152 centimeter). The second criterion is that the capillary base diameter be small enough to allow an expected liquid droplet to bridge across at least one capillary. This criterion is satisfied by the above dimensions for disposable diapers and sanitary items.

The height of the tapered capillary is defined as the distance between the outermost surface of the topsheet (i.e., that surface which normally contacts the skin of the user) and the apex of the tapered capillary. This height, of course, depends upon apex diameter, base diameter, and angle of taper which have been selected as hereinbefore described. The height of the tapered capillary should provide a structure with a minimum tendency to collapse in use. The characteristics of the material of construction of the topsheet in large measure determine suitable ranges for the height. When the topsheet is low density polyethylene of from 0.001 to 0.002 inch (0.003 to 0.005 cm) thickness and apex diameter and base diameter are in the preferred range, and angle of taper $\alpha$ is in its critical range, the height of the tapered capillary can be from about 0.003 to about 0.159 inch (0.008 to 0.404 centimeter).

A state of relative dryness on the surface of the topsheet implies that most of the liquid which contacts the topsheet is transferred through it to the fluid absorbent element. This in turn implies that each isolated droplet of fluid in contact with the topsheet must be in contact with the base diameter of a tapered capillary. This state of affairs can best be achieved if the land area (the area of the topsheet that exists between the bases of the tapered capillaries) is maintained at a minimum. The minimum limiting value is the case where conical tapered capillaries or pyramidal tapered capillaries are provided in close packed array (where the periphery of the base of each capillary is in contact on all sides with the periphery of the base of adjacent capillaries). The preferred arrangement of minimum land area tends to insure that an individual droplet will contact at least one tapered capillary. A preferred arrangement in disposable diapers is where the tapered capillaries as hereinbefore described are in ordered arrangement with from about 30 to about 1500 tapered capillaries per square inch of topsheet (5 to 231 per square centimeter).

U.S. Pat. No. 4,629,643, Curro and Linman, issued Dec. 16, 1986, discloses a microapertured polymeric film with improved tactile impression, which can also be used in the practice of this invention.

A highly-preferred fluid-permeable formed-film sheet material which can be employed in the practice of this invention is disclosed in U.S. Pat. No. 4,463,045, Ahr et al., issued Jul. 31, 1984, and reference can be made to that patent to further assist visualization of the Ahr et al. structures.

In general terms, the sheets provided by U.S. Pat. No. 4,463,045, supra, are designed not only to provide a desirable cloth-like tactile impression, but also to substantially eliminate surface gloss. Thus, sheets made of plastic do not have an undesirably shiny, "plasticky" appearance.

"One-way" sheets whose back faces are treated with hydrophilic latex are described in U.S. Pat. No. 4,735,843, Noda, issued Apr. 5, 1988, and these can also be employed herein.

In addition to the sophisticated apertured materials mentioned hereinabove, the practice of the present invention may also be undertaken with hydrophobic sheet materials having simple holes punched therethrough.

It will be understood from the foregoing that the aforesaid, preferred, "sheet" or "film" materials used in the practice of this invention are substantially different from fibrous nonwoven materials, which are characterized by a large number of fibers which overlap each other throughout the thickness of the material. Moreover, such sheet materials are made from materials (preferably, hydrophobic thermoplastic polymeric materials) which provide a clean-appearing, stain-resistant or "non-staining" surface, in use.

Other topsheet materials which can be used herein include, for example, various nonabsorbent fibrous or filamentous network sheets which are aqueous-fluid-permeable by virtue of a multiplicity of holes or channels passing therethrough. Such sheet materials can be prepared by methods well-described in the patent literature. For example, according to the process of U.S. Pat. No. 4,636,419, Madsen et al., issued Jan. 13, 1987, sheets comprising a network of ribboned filaments of two dissimilar chemical types, and with two dissimilar melting or softening points, are contacted and cooled to allow the formation of a network sheet characterized by said different transverse and longitudinal polymer materials. Such sheets can be used in the practice of this invention.

Another sheet material useful herein is the foraminous net comprising a reticular network of polymeric filaments, said net comprising two arrays of filaments oriented at a displacement angle of 20–90 degrees. Reference can be made to European Pat. Application 0215417, Sneyd et al., filed Sep. 6, 1986, to further assist visualization of this sheet. The aforesaid sheet materials can be prepared using hydrophobic plastics such as polyethylene, polypropylene, PVC, and the like, and are well-known for use in absorbent products such as catamenials, and the like. Such sheet materials typically have a basis weight of 0.5–5.0 ounces/yd$^2$(0.0016 g/cm$^2$–0.016 g/cm$^2$), a caliper of 5–25 mils, an open area of 30–80% and a mesh of 20–40.

The size of topsheet is dictated by the product design and the size of the wearer. It can be ascertained by those skilled in the art.

II. C Backing Sheet

One major function of the backing sheet (or backsheet) is to prevent body fluids from escaping from, e.g., disposable diaper or catamenial products, and soiling the wearer's outer garments and other surfaces in contact with said products. Any compliant, non-irritating, planar material which is impermeable to body fluids can be used as backsheet. Suitable materials are described with particularity in the hereinbefore incorporated patents and patent application. A preferred backsheet is formed from polyethylene film having a thickness of from about 0.001 to about 0.5 mm, preferably from about 0.012 to about 0.051 mm.

Flushable or biodegradable backing sheets can also be used, e.g., with pantiliner devices herein.

The size of the backsheet is dictated by the exact product design selected and the size of the intended wearer; it can be readily ascertained by those skilled in the art.

II. D. Optional Retaining Means

The fluid absorbent structures herein can optionally, but preferably, be provided with means to hold them in place on or near the user's body to allow the structures to perform their intended function. For example, diapers and incontinence garments can be provided with well-known commercially-available tape fasteners. Sanitary napkins can be provided with glue stripes facing outward on their backsheet in well-known fashion. Various pins, clips and fasteners of well-known types can optionally be employed. The retaining means also provide an additional benefit in that they can contain the body fluids in a more enclosed space. As a consequence, the malodor is also contained and more readily absorbed and removed by the solubilized cyclodextrin.

II. E. Incorporation of Cyclodextrin into Absorbent Articles

Small particle size, uncomplexed cyclodextrin can be applied to the fluid absorbent articles by uniformly sprinkling, mixing, or distributing the cyclodextrin powder onto the fluid absorbent materials.

However, it is commonly known that when in use, the body fluid is not normally distributed to the whole fluid absorbent article, e.g., diaper, but usually localized in a portion of the article. Actually, modern disposable diapers are designed with a concentration of the fluid absorbent material at different locations depending on the sex of the wearers. Similarly, it is not necessary to apply the uncomplexed cyclodextrin to the entire fluid absorbent article. Preferably, uncomplexed cyclodextrin powder is applied to areas most likely to be wetted by body fluids to avoid waste in the areas which do not normally receive the body fluids.

Furthermore, when distributed as a dry powder, the cyclodextrin particles may shift away from the preferred locations, and moved to the areas where they have less chance to be solubilized by the body fluids, and become less effective. The shifting happens both during the manufacturing processes, e.g., folding, and packaging of the articles, and during later steps, e.g., transportation, and unfolding and refolding of the fluid absorbent article in use. Therefore, it is preferred to provide a means to immobilize the uncomplexed cyclodextrin powder to the preferred locations in the fluid absorbent articles.

One preferred method is an in situ and rapid crystallization wherein the fluid absorbent materials and/or nonwoven topsheets are impregnated with a saturated aqueous solution of uncomplexed beta-cyclodextrin. Upon drying, the cyclodextrin crystallizes out as small particles adhering to the absorbent material and is immobilized on said material. This can be done small-scale in the laboratory by applying, e.g., spraying, the cyclodextrin solution onto the already formed and dry absorbent fiber web, or in a production plant where the cyclodextrin or its solution is treated on the wet fiber web. For the gellant, it is preferred to apply the cyclodextrin solution to the wet gellant when it is made in the plant.

Another preferred method is to use a water-soluble binder to attach the cyclodextrin powder to the fluid absorbent materials and/or topsheets. The water-soluble binders are preferably polymeric. They can be low melting polymers such as polyethylene glycols (PEG), poly(ethylene glycol) methyl ethers, or mixtures thereof. They can also be high melting polymers such as polyvinyl alcohols, polyacrylic acids, or polyvinylpyrrolidone.

Preferred low melting water-soluble PEG materials have the general formula RO—(CH$_2$CH$_2$O)$_n$—R wherein each R is a hydrogen radical, a C$_1$–C$_4$ alkyl radical, or mixtures of such radicals, and have an average molecular weight (NW) of from about 600 to about 20,000 (n is from about 13 to about 450). More preferred PEG materials are polyethylene glycols, poly(ethylene glycol) methyl ethers, or mixtures thereof, with MW of from about 1,000 to about 9,000 (n from about 20 to about 200), more preferably from about 1,400 to about 4,500 (n from about 30 to about 100). The weight ratio of the uncomplexed cyclodextrin to the PEG material is from about 3:1 to about 1:5, preferably from about 2:1 to about 1:3.

A preferred process of attaching cyclodextrin powder involves admixing solid uncomplexed small-particle-sized cyclodextrin powder with a molten hydrophilic PEG material. The molten mixture can be sprayed directly to the dry fluid absorbent materials or topsheets, then letting the droplets solidify on said materials or nonwoven topsheets. Another preferred method is to pulverize the solidified cyclodextrin/binder mixture into small particles first. Said particles can then be attached and immobilized to the surface of the fluid absorbent materials or the nonwoven topsheets by distributing the particles on said surface, melting said particles by, e.g., a heat source, and then resolidifying to bind said particles to said surface. At the cyclodextrin to the PEG material weight ratio of from about 3:1 to about 1:3, the molten mixture can be solidified to room temperature then pulverized at room temperature or cryogenically. At the uncomplexed cyclodextrin to the PEG material weight ratio of from about 1:2 to about 1:5, the molten mixture can be prilled by, e.g., spray drying, marumarizing, etc., into solid prills. The solid uncomplexed cyclodextrin/PEG material mixture particles preferably have sizes of from about 10 microns to about 1,000 microns, more preferably from about 20 microns to about 600 microns.

Another preferred process comprises blending the uncomplexed cyclodextrin powder with an aqueous solution of a high melting, water-soluble polymer, such as polyvinyl alcohols, polyacrylic acids, and polyvinylpyrrolidone. The aqueous mixture is distributed, e.g., by spraying, to the fluid absorbent materials or the nonwoven topsheets, then the resulting combination is dried, and thus attaching the cyclodextrin to said fluid absorbent materials or topsheets. Preferred MW of said polymers are from about 1,000 to about 200,000; more preferred are from about 2,000 to about 100,000.

It is essential that at least an effective amount of the uncomplexed, small size cyclodextrin be attached to the article. Effective amounts are typically in the range of from about 0.01 g to about 20 g, preferably from about 0.02 g to about 15 g, more preferably from about 0.03 g to about 10 g per article.

The following are non-limiting examples of the forms of uncomplexed cyclodextrin particles that can be used in the present invention.

Cyclodextrin/PEG Particles 1

Solid cyclodextrin/polyethylene glycol particles are prepared as follows. One part of the uncomplexed cyclodextrin with small particle size is mixed thoroughly with about 1 part of molten polyethylene glycol with an average MW of about 3,400, at about 70°. The composition solidifies upon cooling, and is cryogenically ground with dry ice. The resulting solid cyclodextrin/-polyethylene glycol particles are sorted to get particle size of less than about 500 microns.

Cyclodextrin/PEG Particles 2

Solid cyclodextrin/polyethylene glycol particles are prepared as follows. One part of the uncomplexed cyclodextrin with small particle size is mixed thoroughly with about 3 parts of molten polyethylene glycol with an average MW of about 1,450, at about 80°. The molten composition is atomized in a spray drying tower to obtain solid particles. Solid particles solidify on the wall of the tower and are removed for particle size classification. Some particles have sizes larger than about 500 microns are ground further to reduce the particle size by cryogenic grinding with dry ice.

Cyclodextrin/PEG Particles 3

Solid cyclodextrin/polyethylene glycol monomethyl ether particles are made similarly to those of Example 2, using polyethylene glycol mono-methyl ether of average MW of about 5,000.

III. Optional Adjunct Odor-Controlling Materials

The compositions and articles of this invention optionally contain, in addition to uncomplexed, small particle size cyclodextrins, an effective, i.e., odor-controlling, amount of various additional adjunct odor-controlling materials. Incorporating adjunct odor-controlling materials will enhance cyclodextrin's capacity for controlling odors, as well as the range of odor types being controlled. Such materials include, for example, zeolites, activated carbon, kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like. Especially preferred is zeolite material having "intermediate" silicate/aluminate ratios (vide infra). Such materials typically are present at a level of from about 0.01 g to about 15 g, more preferably from about 0.1 g to about 10 g, in fluid absorbent articles of the type disclosed herein to provide additional odor control benefits. Some partially neutralized hydrogel-forming absorbent gelling materials, such as polyacrylate gelling material and acrylate grafted starch gelling material (vide infra), are also useful in the present invention to control certain amine-type odors. These materials are discussed in II. A. under Fluid Absorbent Material because they also function as a substrate for the other odor controlling agents.

III. A. Zeolite Odor-Controlling Agent

In general terms, traditional zeolites comprise an aluminate/silicate framework, with associated cations, M, providing overall electrical neutrality. Empirically, the zeolite framework can be represented as x $AlO_2$.y $SiO_2$ and the electrically neutral zeolite as x/n M.x $AlO_2$.y $SiO_2$.z $H_2O$ wherein: x and y are each integers, M is a cation and n is the charge on the cation. As noted by the empirical formula, zeolites may also comprise waters of hydration (z $H_2O$). M can be a wide variety of cations, e.g., $Na^+$, $K^+$, $NH_4^+$, alkylammonium, heavy metals, and the like.

A preferred class of zeolites useful in the present invention is characterized as "intermediate" silicate/aluminate zeolites. The "intermediate" zeolites are characterized by $SiO_2/AlO_2$ molar ratios of less than about 10. Typically, the molar ratio of $SiO_2/AlO_2$ will range from about 2 to about 10. The intermediate zeolites have three advantages over "high" zeolites, disclosed in U.S. Pat. Nos. 4,795,482 and 4,826,497, which are incorporated herein by reference. First, the intermediate zeolites have a higher capacity for amine-type odors which is important for controlling urine and menses odors. Second, the intermediate zeolites have a larger surface area (700–800 $m_2$/g) than high zeolites (about 400 $m_2$/g). Therefore, less intermediate zeolite is needed to absorb a given amount of odor on a weight to weight basis. Third, intermediate zeolites are more moisture tolerant and retain more odor-absorbing capacity in the presence of water.

A wide variety of intermediate zeolites suitable for use herein are commercially available as VALFOR CP301-68, VALFOR 300-63, VALFOR CP300-35 and VALFOR CP300-56, from P Q Corporation, and the CBV100 series (other than Mordenite, as noted below) of zeolites from Conteka.

The zeolites used herein are not of the fibrous type, e.g., various Mordenites, and some types of Y zeolites, since these may cause asbestos-type safety issues. Accordingly, the term "zeolite" as used herein is intended to encompass only the non-fibrous zeolites. While some naturally-occurring zeolites meet the objectives of this invention, the synthetic zeolites of the types available in commerce are generally more preferred.

Even though intermediate zeolites are preferred, high zeolites can be optionally employed in the practice of this invention in combination with the intermediate ratio zeolites. High zeolites include, for example, the well-known "molecular sieve" zeolites of the ZSM, beta zeolite, etc., type (generally in the 1–10 micron particle size range) and the zeolite materials marketed under the trade name ABSCENTS by the Union Carbide Corporation and UOP. ABSCENTS are typically available as a white powder in the 3–5 micron particle size range (See: ABSCENTS, A New Approach for Odor Control by A. J. Gioffre, copyright 1988 by the Union Carbide Corporation). Such materials are preferred over the "intermediate" zeolites for control of odors associated with sulfur compounds, e.g., thiols, mercaptans.

Various other modified zeolite-type materials which can be used in the present invention, such as the manganese-aluminum-phosphorus-silicon-oxide molecular sieves and other zeolite odor-controlling compositions, are described in U.S. Pat. No. 4,793,833, Lok et al., U.S. Pat. Nos. 4,604,110, 4,437,429, and 4,648,977, which are incorporated herein by reference.

III. B. Carbon Odor-Controlling Agent

The carbon material employed herein is the material well known in commercial practice as an adsorbent for organic molecules and/or for air purification purposes. Carbon suitable for use herein is available from a variety of commercial sources under trade names such as CALGON Type "CPG", Type "PCB," Type "SGL", Type "CAL", and Type "OL". Often, such carbon material is referred to simply as "activated" carbon or "activated" charcoal. Typically, it is available in the form of extremely fine, dusty particles (e.g., about 0.1–300 microns) having large surface areas (about 200 to several thousand m$^2$/g). It is to be understood that any of the "air purifying" or "activated" carbons of commerce can be used in the practice of this invention.

In the event the zeolites herein are optionally to be used in conjunction with the activated carbon, it is preferred (for aesthetics reasons) to coat the carbon with the zeolite using a binder.

III. C. Other Adjunct Odor-Controlling Agent

Other odor-controlling agents include kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like.

IV. Optional Moisture-Activated Encapsulated Perfume

The compositions and articles of this invention contain optionally an effective amount of various moisture-activated encapsulated perfume particles. Such materials include, for example, cyclodextrin/perfume inclusion complexes, polysaccharide cellular matrix perfume microcapsules, and the like. In these materials the perfumes are contained and kept from interacting with and from depleting the odor-absorbing materials before the product is used, and are released when the materials are wetted, to provide a pleasant odor signal in use. Especially preferred are cyclodextrin inclusion complexes of volatile perfumes, with particle size of less than about 12 microns.

IV. A. Perfumes

The perfume ingredients and compositions of this invention are the conventional ones known in the art. Selection of any perfume component, or amount of perfume, is based on functional and aesthetic considerations. Preferred perfume components useful in the present invention are the highly volatile, and the moderately volatile perfume ingredients, more preferably the highly volatile, low boiling ingredients.

The highly volatile, low boiling, perfume ingredients typically have boiling points of about 250° C. or lower. These highly volatile perfume ingredients are fleeting and are quickly lost as they are released. Many of the more moderately volatile perfume ingredients are also quickly lost. The moderately volatile perfume ingredients are those having boiling points of from about 250° C. to about 300° C. Many of the perfume ingredients as discussed hereinafter, along with their odor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

IV. B. Perfume Inclusion Complexes Formation

The perfume/cyclodextrin inclusion complexes of this invention are formed in any of the ways known in the art. Typically, the complexes are formed either by bringing the perfume and the cyclodextrin together in a suitable solvent, e.g., water, or, preferably, by kneading/slurrying the ingredients together in the presence of a suitable, preferably minimal, amount of solvent, preferably water. The kneading/ slurrying method is particularly desirable because it results in smaller particles so that there is less, or no, need to reduce the particle size. In addition, less solvent is needed and therefore less separation of the solvent is required. Disclosures of complex formation can be found in Atwood, J. L., J. E. D. Davies & D. D. MacNichol, (Ed.): *Inclusion Compound, VOL. III*, Academic Press (1984), especially Chapter 11, Atwood, J. L. and J. E. D. Davies (Ed.): *Proceedings of the Second International Syposium of Cyclodextrins* Tokyo, Japan, (July, 1984), and J. Szejtli, *Cyclodextrin Technology*, Kluwer Academic Publishers (1988), said publications incorporated herein by reference.

In general, perfume/cyclodextrin complexes have a molar ratio of perfume compound to cyclodextrin of about 1:1. However, the molar ratio can be either higher or lower, depending on the size of the perfume compound and the identity of the cyclodextrin compound. The molar ratio can be determined by forming a saturated solution of the cyclodextrin and adding the perfume to form the complex. In general the complex will precipitate readily. If not, the complex can usually be precipitated by the addition of electrolyte, change of pH, cooling, etc. The complex can then be analyzed to determine the ratio of perfume to cyclodextrin.

As stated hereinbefore, the actual complexes are determined by the size of the cavity in the cyclodextrin and the size of the perfume molecule. Desirable complexes can be formed using mixtures of cyclodextrins since perfumes are normally mixtures of materials that vary widely in size. It is usually desirable that at least a majority of the material be alpha-, beta-, and/or gamma-cyclodextrin, more preferably beta-cyclodextrin. The content of the perfume in the beta-cyclodextrin complex is typically from about 5% to about 15%, more preferably from about 7% to about 12%.

Continuous complexation operation usually involves the use of supersaturated solutions, kneading/slurrying method, and/or temperature manipulation, e.g., heating and then either cooling, freeze-drying, etc. The complexes are dried to a dry powder to make the desired composition. In general, the fewest possible process steps are preferred to avoid loss of perfume.

IV. C. Complex Particle Size

The small particles of this invention, e.g., those having a particle size of less than about 12 microns, preferably less than about 10 microns, more preferably less than about 8 microns, and even more preferably less than about 5 microns, are desirable for improving the release, especially the speed of release, of the perfume when the complexes are wetted.

The particle size is typically between about 0.001 and 10 microns, preferably between about 0.05 and 5 microns. It is highly desirable that at least an effective amount of the perfume be in complexes having the said particle sizes. It is desirable that at least about 75%, preferably at least about 80% and more preferably at least about 90% of the complex that is present have the said particle sizes. It is even better if essentially all of the complex has the said particle sizes.

These small particles of the invention are conveniently prepared by kneading methods and/or grinding techniques. Cyclodextrin complexes with large particle sizes can be pulverized to obtain the desired smaller particles of less than about 12 microns by using, e.g., a fluid energy mill. Examples of fluid energy mills are the Trost Air Impact Pulverizers, sold by Gatlock Inc., Plastomer Products, Newtown, Pa.; the Micronizer fluid energy mills sold by Sturtevant, Inc., Boston, Mass.; and the Spiral Jet Mill sold by Alpine Division, MicroPul Corporation (Hosokawa Micron International, Inc.), Summit, N.J.

As used herein, the particle size refers to the largest dimension of the particle and to the ultimate (or primary) particles.

Methods for determination of particle sizes of the cyclodextrin/perfume inclusion complexes are similar to those for uncomplexed cyclodextrin particles, vida supra. Care should be taken to avoid contact of the cyclodextrin/perfume complex particles with an excessive amount of water to prevent unwanted particle dissolution and perfume release.

IV. D. Incorporation of Cyclodextrin /Perfume Complex

Particles into Absorbent Articles

Small particle size cyclodextrin/perfume complex particles can be applied to the fluid absorbent articles similarly to the application of uncomplexed cyclodextrin particles, as described hereinbefore. The dry cyclodextrin/perfume complex powder can be sprinkled, mixed or distributed onto the fluid absorbent materials. It is also preferred to have the cyclodextrin/perfume complex powder applied to areas where there is the most chance to have contact with the body fluids or other malodor-generating fluids. Similarly, it is preferred to provide a means to immobilize the cyclodextrin/perfume complex particles to the preferred locations in the fluid absorbent articles. Unlike the case of uncomplexed cyclodextrin powder, the immobilization methods for the cyclodextrin/perfume complex powder should not involve an excessive amount of water, to avoid premature release of perfume before the article is used.

A preferred process of attaching cyclodextrin/perfume complex powder to the substrates is the use of a water-soluble binder, preferably a low melting polymeric binder. Preferred binders are polyethylene glycols (PEG), poly (ethylene glycol) methyl ethers, and mixtures thereof, as disclosed hereinbefore for uncomplexed cyclodextrin powder.

Another preferred method is to apply the cyclodextrin/perfume complex slurry to the fluid absorbent materials and/or nonwoven topsheets. Upon drying, the small particles of the cyclodextrin complex adhere to the absorbent material and are immobilized on said material. This can be done, e.g., by spraying the cyclodextrin/perfume complex slurry onto the already formed and dry absorbent fiber web. It is also preferred to add a water-soluble polymeric binder to the complex slurry after the complex has been formed and before the slurry is applied to the substrate.

The optional perfume signal is obtained by incorporating at least an effective amount of the small size cyclodextrin/perfume complex particles into the article. Effective amounts are typically in the range of from about 0.005 g to about 10 g, preferably from about 0.01 g to about 3 g, more preferably from about 0.03 g to about 1 g, per article.

Following are non-limiting examples of the forms of cyclodextrin/perfume complexes that can be incorporated in the article of the present invention.

A perfume used in the following examples is as follows:

Volatile Perfume Composition

| Component | Wt. % |
| --- | --- |
| Alpha Pinene | 5.0 |
| Cedarwood Terpenes | 20.0 |
| Dihydro Myrcenol | 10.0 |
| Eugenol | 5.0 |
| Lavandin | 15.0 |
| Lemon Oil CP | 10.0 |
| Orange Terpenes | 15.0 |
| Phenyl Ethyl Alcohol | 20.0 |
| Total | 100.0 |

Complex 1

A mobile slurry is prepared by mixing about 1 kg of beta-cyclodextrin and about 1,000 ml of water in a stainless steel mixing bowl of a KitchenAid mixer using a plastic coated heavy-duty mixing blade. Mixing is continued while about 175 g of the perfume is slowly added. The liquid-like slurry immediately starts to thicken and becomes a creamy paste. Stirring is continued for about 30 minutes. The paste is now dough-like in appearance. About 500 ml of water is added to the paste and blended well. Stirring is then resumed for about an additional 30 minutes. During this time the complex again thickens, although not to the same degree as before the additional water is added. The resulting creamy complex is spread in a thin layer on a tray and allowed to air dry. This produces about 1100 g of granular solid which is ground to a fine power. The complex retains some free perfume and still has a residual perfume odor.

Complex 2

The last traces of water in Complex 1 are removed by freeze drying, after which Complex 1 loses about 1% of its weight. Examination of the complex particles by scanning electron microscopy shows that practically all of the ultimate (primary) particles of the complex have particle sizes less than about 5 microns. The resulting solid is washed with diethyl ether to remove the residual uncomplexed perfume. The last traces of ether are removed in vacuo to give Complex 2 as a white powder which is odorless when dry but produces the fragrance of the perfume when added to water.

Slurry 1

A mobile slurry is prepared by mixing about 600 g of beta-cyclodextrin and 600 ml of water in a stainless steel mixing bowl of a Kitchen Aid® mixer using a plastic coated heavy duty mixing blade. Mixing is continued while about 105 g of the perfume is slowly added. The liquid-like slurry immediately starts to thicken and becomes a creamy paste. Stirring is continued for about 30 minutes. About 1,200 ml of water is slowly added to the slurry with stirring. The stirring continues for about an additional 30 minutes to give a liquid Slurry 1.

Slurry 2

A mobile slurry in prepared similarly to that of Slurry 1, except that the additional 1,200 ml of water contains about 20 g of dissolved polyethylene glycol with molecular weight of about 3,400.

Complex Particles 1

Solid cyclodextrin/perfume complex/polyethylene glycol particles are prepared as follows. One part of Complex 1 is mixed thoroughly with about 1 part of molten polyethylene glycol with an average MW of about 3,400, at about 70°. The composition solidifies upon cooling, and is cryogenically ground with dry ice. The resulting sol id cyclodextrin/ perfume complex/polyethylene glycol particles are sorted to get particle size of less than about 500 microns.

Complex Particles 3

Solid cyclodextrin/perfume complex/polyethylene glycol particles are prepared as follows. One part of Complex 1 is mixed thoroughly with about 3 parts of molten polyethylene glycol with an average MW of about 1,450, at about 80°. The molten composition is atomized in a spray drying tower to obtain solid particles. Solid particles solidify on the wall of the tower and are removed for particle size classification. Particles larger than about 500 microns are ground further to reduce the particle size by cryogenic grinding with dry ice.

IV. E. Matrix Perfume Microcapsules

Water-soluble cellular matrix solid particles containing perfume stably held in the cells. The water-soluble matrix material comprises mainly polysaccharide and polyhydroxy compounds. The polysaccharides are preferably higher polysaccharides of the non-sweet, colloidally-soluble types, such as natural gums, e.g., gum arabic, starch derivatives, dextrinized and hydrolyzed starches, and the like. The polyhydroxy compounds are preferably alcohols, plant-type sugars, lactones, monoethers, and acetals. The cellular matrix microcapsules useful in the present invention are prepared by, e.g., forming an aqueous phase of the polysaccharide and polyhydroxy compound in proper proportions, with added emulsifier if necessary or desirable, emulsifying the perfumes in the aqueous phase and removing moisture while the mass is plastic or flowable, e.g., by spray drying droplets of the emulsion. The matrix materials and process details are disclosed in, e.g., U.S. Pat. No. 3,971,852, Brennner et al., issued Jul. 27, 1976.

For the purpose of the present invention, it is desirable to have only minimal non-encapsulated surface perfume, preferably of less than about 1%.

Moisture-activated perfume microcapsules can be obtained commercially, e.g., as IN-CAP® from Polak's Frutal Works, Inc., Middletown, N.Y.; and as Optilok System® encapsulated perfumes from Encapsulated Technology, Inc., Nyack, N.Y.

Water-soluble matrix perfume microcapsules preferably have size of from about 0.5 micron to about 300 microns, more preferably from about 1 micron to about 200 microns, most preferably from about 2 microns to about 100 microns.

Water-activated matrix perfume microcapsules can be applied to the fluid absorbent articles by uniformly sprinkling, mixing, or distributing the microcapsules onto the fluid absorbent materials. It is preferred to have the perfume microcapsules applied to areas most likely to be wetted by the body fluids.

An example of water-activated matrix perfume microcapsules is an IN-CAP microcapsule sample (hereinafter called Microcapsule 1), obtainable from Polak's Frutal Works, Inc., having about 50% perfume loading and particle size range of from about 3 microns to about 100 microns. Major components of the perfume are highly volatile components, such as citral and d-limonene.

As an optional component, at least an effective amount of the water-activated matrix perfume microcapsules is applied to the article. Effective amounts are typically in the range of from about 0.001 g to about 5 g, preferably from about 0.005 g to about 1 g, more preferably from about 0.01 g to about 0.5 g, per article.

All percentages, ratios, and parts herein, in the Specification, Examples, and Claims, are by weight and are approximations unless otherwise stated.

The following are non-limiting examples of the instant compositions, articles, and methods.

EXAMPLE 1

A composition of matter suitable for use as an absorbent pad in diapers, sanitary napkins, and the like comprises a substantially homogeneous blend of the following:

| Ingredient | Wt. % |
| --- | --- |
| Southern Softwood Kraft Cellulose Fibers | 80 |
| Small Particle Size Beta-Cyclodextrin | 20 |
| Total | 100 |

EXAMPLE 2

A pad suitable for use as an absorbent structure in diapers, sanitary napkins, and the like is prepared as follows. One part of beta-cyclodextrin is dissolved in about 10 parts of distilled water at about 70° C. into a clear solution. This solution is sprayed on about 10 parts of Kraft cellulose fibers, and let dry. The resulting pad contains small particles of cyclodextrin which are attached to the cellulose fibers.

EXAMPLE 3

A pad suitable for use as an absorbent structure in diapers, sanitary napkins, and the like is prepared as follows. About 5 parts of beta-cyclodextrin and about 1 part of polyethylene glycol of average MW of about 3,400 are dissolved in about 60 parts of distilled water at about 70° C. into a clear solution. This solution is sprayed on about 50 parts of Kraft cellulose fibers. The water is then removed by freeze drying. The resulting pad contains small particles of cyclodextrin which are attached to the cellulose fibers.

EXAMPLE 4

A composition of matter suitable for use as an absorbent pad in diapers, sanitary napkins, and the like is prepared as follows. About 3 parts of solid Cyclodextrin/PEG Particles 1 are dry mixed with about 10 parts of Kraft cellulose fibers. The resulting mixture is placed in an 80° C. oven for about 5 minutes to attach said particles onto said fibers.

EXAMPLE 5

A composition of matter suitable for use as fluid and odor absorbent materials in diapers, sanitary napkins, and the like is prepared as follows. About 3 parts of solid Cyclodextrin/ PEG Particles 2 are dry mixed with about 10 parts of an acrylic acid grafted starch hydrogel having an average particle size of about 250 microns ("Sanwet IM 1000," from Sanyo Co., Ltd., Japan). The mixture is placed in an 80120 C. oven for 5 minutes to attach said cyclodextrin/polyethylene glycol particles onto said acrylic acid grafted starch hydrogel particles. The mixture is cooled and grouped to produce the absorbent materials.

EXAMPLE 6

A composition of matter suitable for use as an absorbent pad in diapers, sanitary napkins, and the like comprises a substantially homogeneous blend of the following:

| Ingredient | Wt. % |
| --- | --- |
| Southern Softwood Kraft Cellulose Fibers | 76 |
| Small Particle Size Beta-Cyclodextrin | 12 |
| Valfor CP300-56 Intermediate Zeolite | 12 |
| Total | 100 |

EXAMPLE 7

A composition of matter suitable for use as an absorbent pad in diapers, sanitary napkins, and the like comprises a substantially homogeneous blend of the following:

| Ingredient | Wt. % |
| --- | --- |
| Southern Softwood Kraft Cellulose Fibers Small Particle Size | 79 |
| Beta-Cyclodextrin | 20 |
| Complex 2 | 1 |
| Total | 100 |

EXAMPLE 8

A composition of matter suitable for use as an absorbent pad in diapers, sanitary napkins, and the like is prepared as follows. About 2 parts of solid cyclodextrin/PEG Particles 1 and about 1 part of Valfor CP300-56 intermediate zeolite powder are dry mixed with about 10 parts of Kraft cellulose fiber. The resulting mixture is placed in an 80° C. oven for about 5 minutes to attach the cyclodextrin particles onto said fibers.

EXAMPLE 9

A composition of matter suitable for use as fluid and odor absorbent materials in diapers, sanitary napkins, and the like is prepared as follows. About 225 g of commercial polyacrylate AGM ("Drytech 512" from Dow Chemical Co., Midland, Mich.) particles, about 15 g of small particle size beta-cyclodextrin and about 15 g of Valfor CP300-35 intermediate zeolite are mixed and stirred in a rotating tumbler for approximately five minutes. About 70 ml of water is added by spraying over about a five minute period. Then, the mixture is blended for about an additional 30 minutes and dried in an over for about 18 hours at about 60° C. Larger particles (e.g., >850 microns) are milled/ground to smaller particles. About 8 g of Complex Particles 2 are dry mixed with the above particles. The mixture is placed in an 80° C. oven for about 5 minutes to attach said cyclodextrin/perfume complex/polyethylene glycol particles onto said AGM odor absorbent particles.

The mixture is cooled and grouped to produce the absorbent materials.

EXAMPLE 10

A lightweight pantiliner suitable for use between menstrual periods, and which can be disposed of in a toilet (i.e., "flushable") comprises a pad (surface area about 117 $cm^2$; Southern Softwood Kraft (SSK) air felt about 3.0 g, containing about 1.0 g of small particle size beta-cyclodextrin), said pad being interposed between the topsheet of U.S. Pat. No. 4,463,045, supra, and a fibrous, nonwoven, flushable backsheet.

EXAMPLE 11

A catamenial product in the form of a sanitary napkin having two flaps extending outward from its absorbent core is prepared using the pad of Example 1 (surface area about 117 cm$^2$; about 8.5 g SSK air felt; about 2.13 g beta-cyclodextrin with small particle size), per the design of U.S. Pat. No. 4,687,478, Van Tillburg, issued Aug. 18, 1987. The non-glossy sheet of U.S. Pat. No. 4,463,045, supra, is used as the topsheet.

EXAMPLE 12

A disposable baby diaper using the odor-control pad of Example 1 is prepared as follows. The dimensions listed are for a diaper intended for use with a child in the 6–10 kilogram size range. These dimensions can be modified proportionately for different size children, or for adult incontinence briefs, according to standard practice.

1. Backsheet: from about 0.025 to about 0.070 mm polyethylene; width at top and bottom about 33 cm; notched inwardly on both sides to a width-at-center of about 28.5 cm; length about 50.2 cm.

2. Topsheet: tapered capillary polyethylene topsheet, per U.S. Pat. No. 3,929,135, described hereinabove; width at top and bottom about 33 cm; notched inwardly on both sides to a width-at-center of about 28.5 cm; length about 50.2 cm.

3. Absorbent core: air-laid wood pulp fibers per Example 1; Taber stiffness range about 7–9.5, about 8.4 mm thick, calendered; width at top and bottom about 28.6 cm; notched inwardly at both sides to a width-at-center of about 10.2 cm; length about 44.5 cm; about 3.2 g of small particle size beta-cyclodextrin dispersed in said core.

4. Elastic leg bands: four individual rubber strips (2 per side); width about 4.77 mm; length about 370 mm; thickness about 0.178 mm (all the foregoing dimensions being n the relaxed state).

The diaper of Example 12 is prepared in standard fashion by positioning the core-plus-odor control material covered with the topsheet on the backsheet and gluing.

The elastic bands (designated "inner" and "outer," corresponding to the bands closest to, and farthest from, the core, respectively) are stretched to about 50.2 cm and positioned between the topsheet/backsheet along each longitudinal side (2 bands per side) of the core. The inner bands along each side are positioned about 55 mm from the narrowest width of the core (measured from the inner edge of the elastic band). This provides a spacing element along each side of the diaper comprising the flexible topsheet/backsheet material between the inner elastic and the curved edge of the core. The inner bands are glued down along their length in the stretched state. The outer bands are positioned about 13 mm from the inner bands, and are glued down along their length in the stretched state. Since the topsheet/backsheet assembly is flexible, the glued-down bands contract to elasticize the sides of the diaper.

EXAMPLE 13

A disposable baby diaper is made similarly to that of Example 12, except that the absorbent core comprises a pad of wood pulp fibers per Example 6, containing about 2 g of small particle size beta-cyclodextrin and about 2 g of intermediate zeolite powder dispersed in said core.

EXAMPLE 14

A disposable baby diaper is made similarly to that of Example 12, except that the absorbent core comprises a pad of wood pulp fibers of Example 7, containing about 3.2 g of small particle size beta-cyclodextrin and about 0.16 g or cyclodextrin/perfume Complex 2.

EXAMPLE 15

A disposable baby diaper is made similarly to that of Example 12, except that the absorbent core comprises a pad of wood pulp fibers of Example 8, containing about 2.6 g of solid Cyclodextrin/PEG Particles 1 and about 1.3 g of intermediate zeolite powder. The zeolite powder is dispersed homogeneously in the core while the cyclodextrin particles are sprinkled onto the dry core, with higher concentration at the central area of the core surface, and the resulting core placed in an 80° C. oven for about 5 minutes to attach the cyclodextrin particles onto the fibers.

EXAMPLE 16

The preparation of a thin sanitary napkin is as follows.

A commercially available trifold wet-laid tissue containing approximately 5 g of absorbent gelling material particles per square foot (which yields about 0.68 g absorbent gelling material per sanitary napkin pad) is used to prepare the core. The trifold tissue laminate is sprayed with a fine mist of water and opened to expose the absorbent gelling material. About 1.2 g of small particle size beta-cyclodextrin is sprinkled onto the AGM. The two sides of the tissue are folded back to their original position, thereby sealing the absorbent gelling material and cyclodextrin inside. The still moist core is resealed by using a hot iron, pressing firmly. About 0.2 g of Complex Particles 2 is sprinkled onto the dry core, with higher concentration at the central area of the core surface. An additional piece of tissue is positioned on top of the core. A hot iron is pressed on top of the tissue to melt and bond the cyclodextrin/perfume complex to the core surface and the tissue.

An absorbent core prepared in the foregoing manner (about 20 cm×7 cm) is placed on top of a slightly larger piece of polyethylene backsheet, with the piece of tissue exposed on top. A formed-film topsheet of the type disclosed in U.S. Pat. No. 4,463,045 is coated evenly on its underside with about 0.03 g of a latex adhesive, and excess adhesive is wiped off. The topsheet is rolled with a glass rod to ensure good contact and proper application of adhesive. The topsheet is then placed on top of the above-prepared core assembly. To ensure good core bonding, the topsheet is weighted with a piece of plexiglas.

The assembly is sealed together to provide the overall product: topsheet/tissue/cyclodextrin complex/absorbent core with odor-controlling components/backsheet. Optionally, adhesive can be applied on the outside of the backsheet of the pad for affixing the article to undergarments. The topsheet of the product is sprayed with about 0.03 g of Pegosperse® nonionic surfactant (PEG 200) to hydrophilize the fluid-receiving surface of the topsheet.

While the foregoing illustrates the preparation of a sanitary napkin in the manner of this invention, an entirely similar operation can be employed to prepare a pantiliner (generally of the dimensions approximately 14 cm×5 cm) with appropriate modifications of the amounts of the ingredients, as noted hereinabove.

When the zeolites are optionally to be used in conjunction with activated carbon, it is preferred (for aesthetics reasons)

to coat the carbon with the zeolite using a binder. The following illustrates this in detail.

Preparation of Carbon/Zeolite/Binder Particles—A simple, yet effective, method for preparing the particles herein employs a fluidized bed coating apparatus.

Fluid Bed Coating—Bottom spray fluid bed (Wurster) is the preferred method: This is an effective way to get a good coating onto an individual particle, because of the ordered flow up the center draft tube and because the flow of the spray and particle are in the same direction. Using bottom spray without the tube with charcoal/zeolite provides a desirable agglomerated particle in the manner of this invention. The lower limit of this process is nominally 100 microns.

Using the Wurster process a preferred particle is made using about 300–500 micron size carbon (CALGON PCB30x140) and about 1–90 micron size intermediate range zeolite (VALFOR; Philadelphia Quartz) with METHOCEL E5 as the binder. This provides the following advantages. Starting with a larger size core particle gives a bigger "target" for the coating spray to hit. The particle flow in the draft tube is probably more regular. Moreover, for the same weight percent of coating, the wall is thicker on a larger core particle. (The surface to area ratio is smaller for a larger particle.) A thicker wall means better masking. In addition, METHOCEL E5 is somewhat tacky and has a high viscosity. While a higher viscosity can limit the ability to atomize and pump-on the coating, it also can mean a stickier coating. Other coatings that are less viscous do not appear to duplicate this effect.

In a representative example, about 100 g of METHOCEL 5E binder are dissolved in about 1900 ml deionized water. Zeolite (VALFOR CP300-56; about 398 g) is added to the METHOCEL solution (about 19.9% dispersion). A high shear mixer (Tekmar High Shear Mixer Model SD45) is used to create a dispersion of the zeolite. Typical shear time is about 15 minutes.

About 996 g of commercial carbon powder are placed in a Wurster Fluid Bed Coater (about 10 cm Ascoat Unit Model 101, Lasko Co., Leominster, Mass.). The carbon material is fluidized in the bed at an air flow of about 18 scfm (standard cubic ft./min.); the inlet temperature is brought to about 138° F. (about 59° C.).

The flow of VALFOR/METHOCEL coating solution into the spray nozzle is begun (¼-Round Spray Nozzle made by The Spraying Systems Co.; 0.40/0.100 fluid cap.; 0.120 air cap.). The flow rate is set at 7.7 g/min. Exit air temperature is about 77°–84° F. (25° to about 29° C.).

In a typical run, particles prepared in the foregoing manner comprise from about 20% to about 50% carbon; from about 20% to about 40% zeolite, the balance comprising the binder. Particle sizes range from about 90 to about 300 microns.

These carbon-containing, zeolite-coated, odor-controlling particles are especially adapted for use in catamenials, especially sanitary napkins, as well as in other disposable sanitary products. The preferred particles herein are of an off-white to gray or light bluish color, and are, thus, rather unobtrusive in the product. The mixture of zeolite-coated carbon particles and particulate absorbent gelling material (especially polyacrylates or starch/acrylates) is easily added to disposable articles. The particle mixture is spread or sprinkled onto a water-permeable paper or nonwoven tissue and covered with a second tissue to form a tissue/particles/tissue laminate structure that is quite thin. The tissue laminate is then placed in the article, generally as a layer directly under the topsheet. Optionally, an absorbent core can underlie the tissue layer, e.g., in a sanitary napkin. For pantiliners, the additional fluid absorbent capacity afforded by the absorbent core is optional, and may not be needed for most uses.) The zeolite/carbon particles control odor and the absorbent gelling material both helps control some odor, plus absorbs body fluids.

The following Example 17 illustrates a preferred tissue/particles/tissue laminate and its use in a sanitary napkin or pantiliner, using the following preferred materials.

1. Carbon—available from Calgon as PCB30x140; average particle size (sieve analysis) ranging from about 100 to about 600 microns, preferably from about 200 to about 500 microns.

2. Zeolite—available as any of the VALFOR series; or zeolite Y (Conteka); average particle size (X-ray analysis) ranging from about 0.2 to about 90 microns.

3. Coating method—Wurster fluidized bed, using METHOCEL E5/water at from about 4% to about 10%, preferably from about 4.5% to about 8.5%, by weight METHOCEL.

4. Weight ratio of zeolite:carbon from about 0.8 to about 1.25, preferably about 1:1.

5. Color—off-white to gray or gray/bluish.

6. Size of zeolite/METHOCEL/carbon particle (sieve analysis, average size) from about 125 to about 825 microns, although particles up to about, 1,000 microns are satisfactory.

7. Absorbent gelling material—polyacrylate or starch/polyacrylate/available as L-74 from Shokubai or as 1180 from NALCO. Average particle sizes range from about 100 to about 350 microns, preferably from about 150 to about 300 microns.

8. Weight ratio of zeolite-coated carbon particles to absorbent gelling material particles—in the range of from about 10:1 to about 1:10, preferably from about 3:1 to about 1:3, most preferably about 1:1.

9. Amount of zeolite-coated carbon particles used per tissue laminate—for sanitary napkins ranging from about 0.05 g to about 1.4 g, preferably at least about 0.2 g. For pantiliners, somewhat less can be used; typically from about 0.05 g to about 0.4g.

10. Amount of absorbent gelling material used per tissue laminate—for sanitary napkins ranging from about 0.2 g to about 1.0 g, preferably at least about 0.5 g. For pantiliners, somewhat less can be used; typically from about 0.3 g to about 0.5 g.

11. Amount of small particle size uncomplexed beta-cyclodextrin used per tissue laminate—from about 0.1 g to about 2 g. 12. Amount of cyclodextrin/perfume complex used per tissue laminate—from about 0.1 g to about 0.5 g.

EXAMPLE 17

The preparation of a thin sanitary napkin is similar to that of Example 16.

A commercially-available trifold wet-laid tissue containing approximately 5 g of absorbent gelling material particles per square foot (which yields approximately 0.68 g absorbent gelling material per sanitary napkin pad) is used to prepare the core. The trifold tissue laminate is sprayed with a fine mist of water and opened to expose the absorbent gelling material. About 0.6 g of small particle size beta-cyclodextrin and about 0.6 g of VALFOR-coated charcoal, prepared by the Wurster coating process (noted above) is sprinkled onto the AGM. The two sides of the tissue are folded back to their original position, thereby sealing the absorbent gelling material and zeolite-coated charcoal inside. The still moist core is resealed by using a hot iron, pressing firmly.

An absorbent core prepared in the foregoing manner (about 20 cm×7 cm) is placed on top of a slightly larger piece of polyethylene backsheet. About 0.2 g of Complex Particles 2 is sprinkled onto the dry core, with higher concentration at the central area of the core surface. An additional piece of tissue is then positioned on top of the Complex Particles and the core. A hot iron is pressed on top of the tissue to melt and bond the cyclodextrin/perfume complex to the core surface and the tissue. A formed-film topsheet is treated and placed on top of the above-prepared core assembly in the same manner as in Example 16.

It will be understood that the practice of the present invention applies not only to human odors, but also to animal odors.

What is claimed is:

1. A composition comprising:
   I. an effective, malodor absorbing amount of free uncomplexed cyclodextrin, having a particle size of less than about 12 microns;
   II. an effective, fluid-absorbing amount of substrate material selected from the group consisting of fibrous absorbent material, absorbent gelling material, absorbent foam, absorbent sponges, and mixtures thereof;
   III. optionally, an effective, odor-controlling amount of adjunct agent selected from the group consisting of:
      A. zeolite;
      B. activated carbon;
      C. kieselguhr;
      D. water-soluble antibacterial compound; and
      E. mixtures thereof; and
   IV. optionally, moisture-activated encapsulated perfume wherein said encapsulation contains said perfume and keeps said perfume from interacting with said uncomplexed cyclodextrin.

2. The composition of claim 1 wherein a major portion of the uncomplexed cyclodextrin has a particle size of less than about 10 microns.

3. The composition of claim 2 wherein a major portion of the uncomplexed cyclodextrin has a particle size of less than about 8 microns.

4. The composition of claim 3 wherein a major portion of the uncomplexed cyclodextrin has a particle size of less than about 5 microns.

5. The composition of claim 2 wherein a major portion of the cyclodextrin is a mixture of alpha-, beta-, and gamma-cyclodextrin.

6. The composition of claim 5 wherein a major portion of the cyclodextrin is beta-cyclodextrin.

7. The composition of claim 1 wherein the fibrous absorbent material is selected from the group consisting of cotton fluff, cellulose pulp, chemithermomechanical pulp, citric acid cross-linked cellulose pump, synthetic fibers, and mixtures thereof.

8. The composition of claim 1 wherein the absorbent gelling material is selected from the group consisting of:
   (a) hydrolyzed polyacrylate gelling material;
   (b) hydrolyzed polyacrylate grafted starch gelling material;
   (c) hydrolyzed polyacrylonitrile grafted starch;
   (d) maleic anhydride-isobutylene copolymers; and
   (e) mixtures thereof.

9. The composition of claim 8 wherein the absorbent gelling material is (a), (b), and mixtures thereof.

10. The composition of claim 1 wherein the adjunct odor-controlling agent is intermediate silicate/aluminate zeolite having a $SiO_2/AlO_2$ molar ratio of less than about 10.

11. The composition of claim 10 wherein the adjunct odor-controlling agent is a mixture of activated carbon and zeolite.

12. The composition of claim 11 wherein the carbon is coated with the zeolite.

13. The composition of claim 1 wherein the moisture-activated encapsulated perfume is cyclodextrin/perfume inclusion complex.

14. The composition of claim 13 wherein the perfume is selected from the group consisting of highly volatile perfume, moderately volatile perfume, and mixtures thereof.

15. The composition of claim 14 wherein the perfume is highly volatile perfume.

* * * * *